United States Patent [19]

Lamberti et al.

[11] Patent Number: 5,030,751

[45] Date of Patent: Jul. 9, 1991

[54] PROCESS FOR THE PREPARATION OF MIXED 2,2'-OXYDISUCCINATE/CARBOXYME-THYLOXYSUCCINATE

[75] Inventors: Vincent Lamberti, Upper Saddle River; Eddie N. Gutierrez, Ridgefield, both of N.J.

[73] Assignee: Lever Brothers Company, division of Conopco, Inc., New York, N.Y.

[21] Appl. No.: 446,907

[22] Filed: Dec. 6, 1989

[51] Int. Cl.$^5$ ............................................. C07C 51/00
[52] U.S. Cl. .................................................... 562/583
[58] Field of Search ........................................ 562/583

[56] References Cited

U.S. PATENT DOCUMENTS

| | | | |
|---|---|---|---|
| 3,128,287 | 4/1964 | Berg et al. | 562/583 |
| 3,635,830 | 1/1972 | Lamberti et al. | 252/152 |
| 3,692,685 | 9/1972 | Lamberti et al. | 562/583 |
| 3,821,296 | 6/1974 | Blumbergs | 562/583 |
| 3,914,297 | 10/1975 | Lamberti et al. | 562/583 |
| 4,243,820 | 1/1981 | Lamberti et al. | 562/583 |
| 4,798,907 | 1/1989 | MacBrair et al. | 562/583 |

FOREIGN PATENT DOCUMENTS 0236007  9/1987  European Pat. Off. .

*Primary Examiner*—Paul J. Killos
*Attorney, Agent, or Firm*—Rimma Mitelman

[57] ABSTRACT

A process for the preparation of mixed salts of oxydisuccinate/carboxymethyloxysuccinate is disclosed, which process comprises adding glycolic acid to an aqueous mixture obtained from a 2,2'-oxydisuccinate forming reaction. The mixed oxydisuccinate carboxymethyloxysuccinate salts are obtained in high yields and can be used as detergent builder in cleaning compositions.

15 Claims, No Drawings

PROCESS FOR THE PREPARATION OF MIXED 2,2'-OXYDISUCCINATE/CARBOXYMETHYLOXYSUCCINATE

BACKGROUND OF THE INVENTION

1. Field of the Invention

The invention relates to a process for the preparation of mixed salts of 2,2,'-oxydisuccinic acid and carboxymethyloxysuccinic acid. The mixed salts of 2,2,'-oxydisuccinic acid and carboxymethyloxysuccinic acid are effective sequestering agents and are useful as builders in detergent compositions for household, institutional and industrial use.

2. Related Art 2,2,'-oxydisuccinic acid (ODS), carboxymethyloxysuccinic acid (CMOS) and their salts are known and are known to have utility as sequestering agents and detergent builders. A disadvantage of ODS and salts thereof as detergent builders is that they are relatively expensive to prepare.

U.S. Pat. No. 3,128,287 to Berg, discloses a preparation of ODS salt by admixing maleic acid with an excess of hydroxide of calcium, barium, magnesium or strontium in the presence of water, then heating the reaction mixture from about one day to about one month at temperatures ranging from 50° C. to reflux temperatures. The process yields a mixture of malic acid and ODS. Example I teaches the preparation of ODS, wherein the aqueous mixture of maleic anhydride and calcium hydroxide is reacted at reflux (100° C.) for 4 days. Subsequently, ODS salt is isolated from the product containing ODS and malic acids salts.

The preparation of CMOS and salts thereof is described in U.S. Pat. Nos. 3,692,685 and 3,914,297 to Lamberti et al. The reaction involves a Michael type addition of glycolic acid to maleic acid in the presence of calcium hydroxide. U. S. Pat. No. 3,692,685 also discloses CMOS and its salts as detergent builders.

U.S. Pat. No. 3,635,830 to Lamberti et al., discloses the process for the preparation of ODS based on the process of Berg. The patent teaches separation/purification of two diastereoisomeric forms of ODS obtained by the Berg process. The patent also discloses detergent compositions with ODS or its salts as detergent builders.

U.S. Pat. No. 4,798,907 to MacBriar et al. discloses an improvement in the ODS-forming processes of Berg and Lamberti et al., wherein an alkali metal hydroxide, e.g. sodium hydroxide, is incorporated into a starting reaction mixture. To produce yields of about 80% ODS the process generally involves reacting the mixed starting materials in water for at least 12 hours at temperatures of about 20–100° C.

European Patent 236,007 to Bush teaches a process for the preparation of ODS similar to the process of the MacBriar patent. Mixtures of inorganic base with water-soluble, inorganic salts of sodium, calcium or mixtures thereof may be used. A particularly preferred reactant combination constitutes maleic acid, malic acid, calcium hydroxide and sodium hydroxide. An ODS yield of about 60% is obtained in about 6 hours.

The MacBriar et al. and Bush patents rely on incorporation of alkali metal hydroxide into the reactant mixture to minimize gelation of the reactants and to increase yields of ODS. Alkali metal hydroxides indeed produce homogeneous solutions, but unlike the alkaline earth metal hydroxides, generate higher pHs and result in a gradual decomposition of ODS to fumarate and malate under the reaction conditions employed by the MacBriar et al. and Bush patents.

The patents referred to above share the same disadvantages: excessive energy requirements or lowered yields of ODS due to gelation of the reaction medium and the presence of unreacted starting materials or side products. There have been different approaches to the problem of increasing the yields of ODS while lowering the production cost and avoiding gelation. However, none of these approaches has been completely satisfactory.

Accordingly, it is an object of the present invention to provide a process for the preparation of the mixed salts of 2,2'-oxydisuccinic acid and carboxymethyloxysuccinic acid (ODS/CMOS). The process comprises forming ODS salt and utilising unreacted starting materials to form CMOS salt. Thus, the amount of unreacted starting materials is decreased and the yield of a usable builder product is increased. The mixed ODS/CMOS salts can be used as a detergent builder or a sequestering agent.

It is a further object of the present invention to provide a process which produces the mixed ODS/CMOS salts and substantially minimizes the gelation of a reaction mixture.

These and other objects and advantages will appear as the description proceeds.

SUMMARY OF THE INVENTION

The attainment of the above objects is made possible by this invention which includes a preparation of the mixed ODS/CMOS salts by a process comprising the steps of:
(i) forming an aqueous mixture containing 2,2,'-oxydisuccinate and maleate;
(ii) forming a reaction mixture comprising:
  1) said aqueous mixture containing said oxydisuccinate and maleate;
  2) glycolate, e.g. obtained from glycolic acid,
  3) an alkaline earth metal hydroxide; and
(iii) reacting by heating said reaction mixture to form a reaction product containing said mixed ODS/CMOS salts.

In its broadest aspect the invention provides a process for synthesizing the mixed ODS/CMOS salts, wherein the aqueous mixture of step (i) can be formed by one of the processes for the preparation of ODS known in the art.

The invention further includes two alternative processes for the preparation of the mixed ODS/CMOS salts in high yields while substantially minimizing gelation of the reaction mixture. According to this aspect of the invention, the preparation of the mixed ODS/CMOS salts comprises either of two processes designated A or B below for forming the aqueous mixture of step (i).

The process A comprises the steps of:
(1) forming an aqueous mixture comprising:
  a) a malate moiety,
  b) a maleate moiety, and
  c) an alkaline earth metal hydroxide,
wherein the mole ratio of a:b is about 1:5 to about 1:1 and the mole ratio of c:(a+b) is about 1.01:1.0 to about 1:2:1.0; and
(2) reacting said aqueous mixture by heating at a temperature not greater than about 75° C. for at least about 5 hours to form a reaction product in which gelation of said aqueous mixture is substantially minimized and which contains the salt of ODS.

The molar ratio of the alkaline earth metal hydroxide to organic reactants (molar sum of malate and maleate) of about 1.01:1.0 to about 1.2:1.0 and the reaction temperature of not greater than about 75° C. are critical for obtaining the ODS salt product in about 5 hours and minimizing gelation of the reaction mixture process.

Whenever one or both of these critical parameters exceed the values recited above, the alternate process B included in this invention still accomplishes the ODS salt preparation in about 5 hours and substantially minimizes gelation of the reaction mixture by virtue of the inclusion into the reaction mixture of a non reactive alkali metal salt of a weak or strong acid. By non reactive alkali metal salt of a strong or weak acid is meant an alkali metal salt that does not participate in the reaction while still inhibiting gelation through electrolyte effects. In the alternate process B the incorporation of this non reactive alkali metal salt into the reaction mixture is critical and permits the molar ratio of the alkaline earth metal hydroxide to the organic reactants to vary from about 1:01:1 to about 2.0:1.0 and reaction temperatures to increase up to about 95° C.

In defining the mixed ODS/CMOS salts forming processes of this invention it is intended to include both batch and continuous processes.

DETAILED DESCRIPTION OF THE INVENTION

The invention discloses the process for the preparation of the mixed salts of ODS/CMOS comprising the steps of:

i) forming an aqueous mixture containing 2,2,'-oxydisuccinate and maleate;

ii) adding glycolic acid and an alkaline earth metal hydroxide to the aqueous mixture to form a subsequent reaction mixture, iii) heating the subsequent reaction mixture to form the mixed ODS/CMOS salts.

The inventive process for the preparation of the mixed ODS/CMOS salts includes as its first step the ODS salt forming process. As noted, any process for the preparation of the ODS salt known in the art is suitable for use in this invention. However, it is preferred in order to lower cost while substantially minimizing gelation of the reaction mixture that the ODS salt forming process A or process B is used as the first step in the preparation of the mixed ODS/CMOS salts.

The processes A and B are outlined as follows:

Process A
(i) An aqueous mixture of:
a) a malate,
b) a maleate,
c) an alkaline earth metal hydroxide, is formed wherein the molar ratio of c:(a+b) is about 1.01:1.0 to about 1.2:1.0; and
(ii) the mixture is heated at temperatures not greater than about 75° C. for at least about 5 hours and produces ODS salt.

Process B
(i) An aqueous mixture of:
a) a malate,
b) a maleate,
c) an alkaline earth metal hydroxide, and
d) a non reactive alkali metal salt of a strong or weak acid is formed wherein the molar ratio of c:(a+b) is about 1.01:1.0 to about 2.0:1.0; and
(ii) the mixture is heated at temperatures not greater than about 95° C. for at least about 5 hours and produces the ODS salt.

By virtue of incorporation of the non reactive alkali metal salt of a strong or weak acid into the starting reaction mixture of Process B a broader range of the molar ratio of alkaline metal hydroxide to malate and maleate and higher reaction temperatures may be used in Process B than in Process A.

The processes A and B for the preparation of the salt of ODS include forming an aqueous mixture of starting reactants containing a malate moiety, a maleate moiety and an alkaline earth metal hydroxide. The malate and maleate moieties are defined by Formulas I and II respectively.

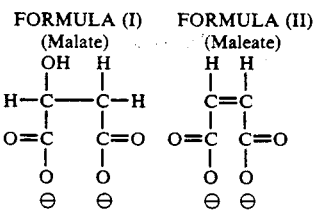

In the aqueous media of the processes herein the malate and maleate would be expected to take anionic forms. The chemically suitable forms of malate and maleate reactants include acids and the anhydride of maleic acid. The molar ratio of Formula I to Formula II is about 1:5 to about 1:1.

The alkaline earth metal hydroxide in the reaction mixtures of the inventive processes is selected from the group consisting of barium hydroxide, strontium hydroxide or calcium hydroxide. The most preferred alkaline earth metal hydroxide for use in this invention is calcium hydroxide.

The ODS salt forming reactions A or B of the present invention are conducted at high concentration in aqueous media to afford efficacy and high throughput. The amount of water present may vary and is preferably sufficient to permit the reaction to proceed with a solute concentration of about 30% to about 75%. The amount may however be more or less depending on design parameters. The non reactive alkali metal salt of Process B is preferably selected from the group consisting of alkali metal chlorides, acetates, xylene sulfonates and the like such as sodium chloride, potassium acetate, sodium xylene sulfonate and mixtures thereof. Preferably, from about 1 to about 10 weight % of the alkali metal salt is used.

When either process A or process B is followed the reaction mixtures characteristically are non-viscous, coarse, powdery suspensions with temperature-corrected pH readings of about 11.5 to 12. The gelation of the reaction mixture upon subsequent heating is substantially minimized. The appearance of the reaction mixtures does not vary significantly over the time of the reaction and the reaction mixtures may be stirred without difficulty.

Desirably, the reactants of the starting mixture for the ODS salt forming reaction A or B are combined in water using physical agitation. In the preferred embodiments of the invention, the alkaline earth metal hydroxide is added to an aqueous mixture of the malate and maleate moieties or the alkaline earth metal hydroxide is added to an aqueous solution of the malate moiety and is followed by addition of the maleate moiety. If the hydroxide is first added to the maleate in the absence of malate, poor yields of ODS will be obtained. The reaction is carried out in an apparatus equipped with stirring means, e.g., on a laboratory scale, a mechanical stirring device or a magnetic stirring bar. The apparatus may also be equipped with a condenser for safety reasons and to provide some means of condensing water which evaporates, so that it returns to the reaction mixture. The reaction is conducted at atmospheric pressure.

The reaction temperature for the A or B process ranges from about 50° C. to about 95° C., preferably from about 65° C. to about 85° C. Whenever the practitioner opts for a reaction temperature greater than about 75° C., the addition of the non reactive sodium salt as recited above in Process B is critical to prevent the gelation of the reactant mixture. To minimize gelation, the reaction temperature is maintained for at least about 5 hours and preferably no longer than about 24 hours.

Other processes for forming the salt of ODS may also be employed, for example, prior art processes such as in the patents described in the Background Art section of this specification. Regardless of whether the A or B processes described herein above or another process known in the art is used as the first step of the mixed ODS/CMOS salt preparation, the aqueous reaction product of this step typically contains a mixture of 2,2,'-oxydisuccinate, malate, maleate and fumarate.

The present process comprises:
(i) forming an aqueous mixture containing 2,2,'-oxydisuccinate and maleate;
(ii) forming a reaction mixture comprising:
  1) said aqueous mixture,
  2) glycolate, e.g. obtained from glycolic acid,
  3) an alkaline earth metal hydroxide; and
(iii) reacting by heating said reaction mixture to form a reaction product containing said mixed ODS/CMOS salts. Desirably, the aqueous mixture which results from the 2,2,'-oxydisuccinate (ODS) salt forming step (i) is analyzed to ascertain the relative amounts of the organic components present. It is particularly desirable to determine the amount of the unreacted maleic acid contained in the mixture.

In the most preferred embodiment of step (ii) of the mixed ODS/CMOS salts forming process the glycolic acid and the alkaline earth metal hydroxide are added with stirring to the aqueous mixture obtained from step (i). Thus, the subsequent aqueous reaction mixture contains, at least: 2,2,'-oxydisuccinate, maleate, glycolate and the alkaline earth metal hydroxide. The terms maleate, glycolate, malate, 2,2,'-oxydisuccinate and the like refer to the corresponding fully anionic moieties derived from maleic acid, maleic anhydride, glycolic acid, malic acid, and 2,2,'-oxydisuccinic acid. The molar ratio of glycolate to maleate is preferably in the range of about 1:1 to about 1.1:1. Most preferably, a slight excess of glycolic acid is used so that the most preferred molar ratio of glycolate to maleate is about 1.1:1. The alkaline earth metal hydroxide is selected from the group consisting of barium hydroxide, strontium hydroxide or calcium hydroxide. Preferably, the pH should be about 11.5 to 12. The most preferred alkaline earth metal hydroxide for use in the step (ii) of the inventive process is calcium hydroxide.

Regardless of the temperature used for the ODS salt forming reaction of step (i), the reaction temperature for step (ii) of the mixed ODS/CMOS salt preparation may range from about 50° C. to about 80° C., preferably from about 65° C. to about 80° C. Most preferably the reaction is conducted at about 75° C. Typically, when a reaction temperature of not greater than about 80° C. under atmospheric conditions is employed, the gelation of the reaction mixture is substantially minimized and high yields of at least about 70% of the mixed ODS/CMOS salts are obtained.

The reaction temperature is maintained for at least about 5 hours and preferably for no longer than about 12 hours.

When the mixed ODS/CMOS salts preparation has been carried out to a desirable extent and at the end of at least about 5 hours the reaction is arrested by cooling to less than 40°C., more preferably to ambient temperature.

The product obtained by the processes of this invention contains the mixed ODS/CMOS salts and may be worked up by methods known in the art. Such methods are disclosed, for example, in U.S. Pat. No. 3,128,287 to Berg and U.S. Pat. No. 3,635,830 to Lamberti et al. discussed above and incorporated herein by reference. Generally, the work up comprises the steps of reduction of calcium content in the product mixture and acidification or conversion into monovalent cation salts, ammonium salts, morpholinium salts, alkanol ammonium salts and mixtures thereof.

The calcium content of the reaction product may be reduced by conventional means. Removal of calcium can be carried out in a number of ways known in the art. In general, simply adding a calcium precipitating material will suffice. Such calcium precipitating materials include, for example, alkali metal carbonate, pyrophosphate, sulfate, bicarbonate and/or alkali metal silicate and mixtures thereof. The resulting calcium precipitate can thereafter be removed from the aqueous reaction product mixture by filtration. In an alternative mode, removing calcium from the aqueous reaction product mixtures involves treatment of said mixtures with an appropriate insoluble ion exchange resin or zeolite. No matter what technique is employed, calcium content of the mixed ODS/CMOS salts prepared by methods herein should desirably be reduced to the extent that calcium is present in an amount of less than about 1.0% of the ODS salt or the mixed ODS/CMOS salts and preferably less than about 0.2% in order to form compositions particularly suitable as detergent builders. A method of reducing the calcium is disclosed in defensive publication T 101,805.

The mixed ODS/CMOS salts formed herein can also be treated, after calcium removal, in a further step, using organic or aqueous solvent extraction to remove excess reactants, such as maleates, or organic reaction by-products, such as fumarates. This can, for example, be accomplished by conventional salt separation procedures using a solvent such as a mixture of methanol and water (4:1 v/v) in which these excess reactants and reaction by-products are relatively soluble and in which the desired ether polycarboxylates are relatively insoluble.

At any stage after the mixed ODS/CMOS salt formation, the reaction product can be concentrated by removal of water to the desired extent. Water removal can, for example, involve substantially complete drying of the reaction product mixture, e.g., by spray drying, so that the mixed ODS/CMOS salts are recovered in solid, e.g., granular, form. Alternatively, the mixed ODS/CMOS salts in the form of aqueous liquids may be utilized directly in the preparation of detergent compositions or laundry additive products of the types more fully described hereinafter.

After reduction of the calcium content in the reaction product mixture, it is possible, if desired, to acidify the product mixture using conventional acidification or ion exchange techniques to convert the mixed ODS/CMOS salts therein to their free acid form. Normally, however, the mixed ODS/CMOS salts of this invention can, after calcium depletion or complete replacement by sodium, be used as builders in their water-soluble salt form, and such acidification is therefore not usually necessary or desirable.

When converted into suitable form, the mixed ODS/CMOS salts can be used as a builder in a wide variety of detergent or laundry additive compositions.

Detergent compositions incorporating the mixed ODS/CMOS salts prepared using the processes of this invention, contain as essential components from about 0.5% to about 98% of a surfactant and from about 2% to about 99.5% of the mixed ODS/CMOS salts as a detergency builder, generally in sodium salt form.

Surfactants that are useful in the present invention are the anionic (soap and nonsoap), nonionic, zwitterionic and ampholytic compounds. The chemical nature of these detergent compounds is not an essential feature of the present invention. Moreover, such detergent compounds are well known to those skilled in the detergent art and the patent and printed literature are replete with disclosures of such compounds. Typical of such literature are "Surface Active Agents" by Schwartz and Perry and "Surface Active Agents and Detergents" by Schwartz, Perry and Berch, the disclosures of which are incorporated by reference herein. The ODS builder can be used either as the sole builder or where desired can be used in conjunction with other well-known builders, examples of which include water-soluble salts of phosphates, pyrophosphates, orthophosphates, polyphosphates, phosphonates, carbonates, polyhdroxysulfonates, polyacetates, carboxylates, polycarboxylates, succinates and the like.

In addition to the surfactant and builder there may be optionally present additional ingredients which enhance the performance of the detergent composition. Typical examples thereof include the well known soil suspending agents, hydrotropes, corrosion inhibitors, dyes, perfumes fillers, optical brighteners, enzymes, suds boosters, suds depressants, germicides, anti-tarnishing agents, cationic detergents, softeners, bleaches, buffers and the like.

The detergent compositions of the present invention may be in any of the usual physical forms for such compositions, such as powders, beads, flakes, bars, tablets, noodles, liquids, pastes and the like. The detergent compositions are prepared and utilized in the conventional manner. The wash solutions thereof desirably have a pH from about 7 to about 12, preferably from about 9 to about 11. At pH values below about 8.6 some of the salts of the oxydisuccinic acid and CMOS will be present in the acid salt form and some in the normal salt form.

In addition to their utility as builders in detergent and laundry additive compositions, the mixed ODS/CMOS salts of the invention can, after reducing their calcium content, also be utilized in other contexts wherein water hardness sequestration is required. Other uses are provided in water softening compositions, devices and methods and boiler descaling compositions and methods.

The following examples are designed to illustrate, but not to limit, the practice of the instant invention. All percentages and parts herein are by weight unless indicated otherwise. All ratios herein are mole ratios unless indicated otherwise.

Reaction mixture samples and reaction products were analyzed by HPLC. The HPLC analysis was carried out using a Hitachi instrument. The mobile phase was a PIC D/4 using phosphoric acid at a pH of about 2. The column is an "octyl reversible" Regis 15 cm ×4.6 mm internal diameter. The flow rate was 1.5 ml/mm at a wavelength of 205 nm.

EXAMPLES 1-5

Examples 1-5 illustrate the critical affect of reaction temperature on increasing the yield of ODS while substantially minimizing gelation of the reaction mixture.

13.4 grams (0.1 mole) malic acid and 65 ml of water were placed into a 100 ml three neck flask. 16.5 grams (0.22 moles) of calcium hydroxide were added to the flask with stirring at 50-60° C. After 2-3 minutes, 9.8 grams (0.1 mole) of maleic anhydride were added to the flask. The mixtures of Examples 1-5 were heated for 6 hours at varying temperatures with samples being removed periodically for NMR analysis. The reaction was terminated after six hours. The reaction mixture was worked up by distilling off the water using a flash evaporator. The reaction products of the acids were analyzed by HPLC. Examples 1-5 at various temperatures are summarized in Table I. The percentages reported are "as is" percentages and are not normalized to 100%. Normalization would make these values higher.

TABLE I

| Example | Reaction Temp. (°C.) | Reaction Product Composition | | | |
|---|---|---|---|---|---|
| | | % ODS | % Malic | % fumaric | % maleic |
| 1 | 60 | 41.0 | 30.6 | 0.36 | 9.7 |
| 2 | 70 | 44.4 | 26.7 | 2.1 | 5.5 |
| 3 | 80 | 36.2 | 31.3 | 5.2 | 4.4 |
| 4 | 90 | 37.4 | 27.8 | 6.1 | 1.8 |
| 5 | 100 | 31.1 | 39.7 | 0.4 | 6.4 |

ODS yield was decreased in Examples 3-5 when reaction temperatures of 80° C., 90° C. and 100° C. were employed compared to Examples 1 and 2 wherein reaction temperatures of 60° C. and 70° C. were employed. Gelation was observed at the higher temperatures of Examples 3, 4 and 5.

EXAMPLE 6

Example 6 illustrates the criticality of maintaining reaction temperature of not greater than about 75° C. to minimize gelation of the reaction mixture. While the conversion to ODS is good, the lumpiness of the reaction mixture due to gelation is extremely undesirable.

13.4 grams (0.1 mole) of malic acid, 75 ml of water and 18 grams (0.24 mole) of calcium hydroxide were placed into 100 ml, three neck flask. The mixture was stirred for 2-3 minutes and 9.8 grams (0.1 mole) of maleic anhydride were added to the flask. The reaction mixture was stirred for 7-8 hours at 75-80° C. The mixture was marginally stirrable and substantial gelation was observed. The reaction product was analyzed by HPLC to contain:

43.5% ODS, 17.0% malic, 3.1% fumaric, and 3.6% maleic.

EXAMPLES 7-9

Examples 7-9 incorporate a non reactive alkali metal salt of a strong or weak acid listed in Table II into the starting reaction mixture as described in the Process B of this specification.

13.4 grams (0.1) mole of malic acid, 60 ml of water and 20 grams (0.27 mole) of calcium hydroxide were placed into a 100 ml, three neck flask. The mixture was stirred well for 2-3 minutes and a non reactive sodium salt of a strong or weak acid listed in Table II was added followed by addition of 9.8 grams (0.1 mole) of maleic anhydride. The mixture was stirred at 75-80° C. for 7-8 hours. No gelation of the reaction mixture was observed. The reaction products of the acids were analyzed by HPLC as in Table I, the percentages are "as is". Examples 7-9 are summarized in Tables II and III.

TABLE II

| Example | Non Reactive Sodium Salt Present In Starting Mixture | Molar Ratio of Calcium Hydroxide to Malate and Maleate | Appearance of Reaction Mixture |
| --- | --- | --- | --- |
| 7 | 0.6 g sodium chloride | 1.35 | No gelation - Some stirrable solid |
| 8 | 5.3 g sodium xylene sulfonate | 1.35 | No gelation |
| 9 | 4.0 g sodium acetate | 1.35 | No gelation |

TABLE III

| | Reaction Product Composition | | | |
| --- | --- | --- | --- | --- |
| Example | % ODS | % Malic | % fumaric | % maleic |
| 7 | 33.2 | 19.3 | 1.7 | 5.7 |
| 8 | 32.5 | 20.0 | 3.3 | 1.5 |
| 9 | 26.2 | 21.0 | 4.3 | 12.3 |

Examples 7-9 illustrate that incorporation of a non reactive alkali metal salt of a strong or weak acid into the starting mixture prevents gelation of the reaction mixture when the ODS salt forming reaction is conducted at temperatures greater than about 75° C. or when the molar ratio of calcium hydroxide to malate and maleate is greater than about 1.0 to 1.2.

EXAMPLE 10

Example 10 illustrates the inventive process for the preparation of the mixed ODS/CMOS salts, wherein a high yield is achieved while gelation of the reaction mixture is substantially minimized.

13.4 grams (0.1 mole) of malic acid were dissolved in 70 ml of water. 16.1 grams (0.218 mole) of Ca(OH)2 were added, and the temperature increased to 50-60° C. The mixture was cooled to 40° C. and 9.8 g (0.1 mole) of maleic anhydride were added. This reaction mixture was heated at 75° C. for 8-9 hours, after which a sample was removed for NMR analysis.

1.4 grams (0.02 mole) of glycolic acid and 0.8 grams (0.01 mole) of calcium hydroxide were added to the reaction mixture. The mixture was stirred at 75° C. for 5 hours. Throughout the reaction no gelation of the reaction mixture was observed. The reaction was arrested by cooling to room temperature. 22 grams of concentrated sulfuric acid were diluted in 22 ml water and the solution was added to the reaction product. The mixture was stirred for an hour and hydrated calcium sulfate was filtered off. The solution containing the reaction product was evaporated to dryness, recovering 27 grams of product. The product mixture was analyzed by HPLC and was found to contain:

% ODS 64.2
% CMOS 7.2
% FUMARIC ACID 5.9
% MALEIC ACID 4.7
% GLYCOLIC ACID 4.7
% MALIC ACID 5.0
% $H_2O$ 8.3

The inventive process for the preparation of the mixed ODS/CMOS salts leads to a high yield of the ODS salt and the mixed ODS/CMOS salts. Also advantageously, the presence of unreacted malic acid is decreased from the levels observed in Examples 1-5 and 7-9.

The foregoing description and Examples illustrate selected embodiments of the present invention and in light thereof variations and modifications will be suggested to one skilled in the art, all of which are in the spirit and purview of this invention.

What is claimed is:

1. A process for the preparation of mixed salts of 2,2,'-oxydisuccinic acid and carboxymethyloxysuccinic acid, said process comprising:
   (i) forming an aqueous mixture comprising 2,2,'-oxydisuccinate and maleate;
   (ii) forming a reaction mixture comprising:
      1) said aqueous mixture,
      2) glycolate, and
      3) an alkaline earth metal hydroxide; and
   (iii) reacting by heating said reaction mixture to form a reaction product which contains said mixed salts of 2,2'-oxydisuccinic acid and carboxymethyloxysuccinic acid.

2. A process as recited in claim 1 wherein the mole ratio of glycolate to maleate is about 1.0:1.0 to about 1.1:1.0.

3. A process as recited in claim 1 wherein the alkaline earth metal hydroxide is calcium hydroxide.

4. A process as recited in claim 1 wherein said reaction mixture is heated at a temperature not greater than about 80° C. for at least about 5 hours to form a reaction product in which gelation of said reaction mixture is substantially minimized and which contains said mixed salts of 2,2,'-oxydisuccinic acid and carboxymethyloxysuccinic acid.

5. A process as recited in claim 4 wherein the yield of said mixed salts of 2,2,'-oxydisuccinic acid and carboxymethyloxysuccinic acid is at least about 70% by weight of the reaction product.

6. A process as recited in claim 1 wherein said aqueous mixture of step (i) is formed by conducting a reaction comprising:
   (1) forming an aqueous mixture comprising:
      a) a malate moiety,
      b) a maleate moiety, and
      c) an alkaline earth metal hydroxide,
      wherein the mole ratio of c:(a +b) is about 1.01:1.0 to about 1.2:1.0; and
   (2) reacting said aqueous mixture by heating at a temperature not greater than about 75° C. for at least about 5 hours to form a reaction product in which gelation of said aqueous mixture is substantially minimized and which contains said 2,2,'-oxydisuccinate.

7. A process as recited in claim 6 wherein said maleate moiety is selected from the group consisting of moieties derived from maleic anhydride, maleic acid and mixtures thereof.

8. A process as recited in claim 6 wherein said malate moiety is malic acid.

9. A process as recited in claim 6 wherein said alkaline earth metal hydroxide is calcium hydroxide.

10. A process as recited in claim 6 wherein the mole ratio of a:b is about 1:5 to about 1:1.

11. A process as recited in claim 1 wherein said aqueous mixture of step (i) is formed by conducting the reaction comprising:

(1) forming an aqueous mixture comprising:
   a) a malate moiety,
   b) a maleate moiety,
   c) an alkaline earth metal hydroxide, and
   d) a non reactive alkali metal salt of a strong or weak acid, wherein the mole ratio of c:(a + b) is about 1.1:1.0 to about 2.0:1.0; and (2) reacting said aqueous mixture by heating at a temperature of at least about 40° C. and not greater than about 95° C. for at least about 5 hours to form a reaction product in which gelation of said aqueous mixture is substantially minimized and which contains said 2,2,'-oxydisuccinate.

12. A process as recited in claim 10 wherein said maleate moiety is selected from the group consisting of moieties derived from maleic anhydride, maleic acid and mixtures thereof.

13. A process as recited in claim 10 wherein said malate moiety is malic acid.

14. A process as recited in claim 10 wherein said alkaline earth metal hydroxide is calcium hydroxide.

15. A process as recited in claim 10 wherein said non reactive alkali metal salt of a strong or weak acid is selected from the group consisting of sodium chloride, sodium acetate or sodium xylene sulfonate.

* * * * *